United States Patent [19]

Regnier et al.

[11] Patent Number: 5,126,356
[45] Date of Patent: Jun. 30, 1992

[54] PIPERIDINE COMPOUNDS

[75] Inventors: Gilbert Regnier, Chatenay Malabry; J. F. Renaud De La Faverie, Le Chesnay; Alain Lombet, Champigny; Jean-Pierre Iliou, Puteaux; Jean-Paul Vilaine, Chatenay Malabry; Jean-Pierre Bidouard, Chilly Mazarin; Albert Lenaers, Triel Sur Seine, all of France

[73] Assignee: Adir et Compagnie, Courbevoie, France

[21] Appl. No.: 625,422

[22] Filed: Dec. 11, 1990

[30] Foreign Application Priority Data

Dec. 12, 1989 [FR] France ................ 89 16384

[51] Int. Cl.$^5$ .................. A61K 31/445; C07D 211/54
[52] U.S. Cl. .................... 514/327; 514/320; 514/324; 546/192; 546/196; 546/202; 546/216; 546/217
[58] Field of Search ............... 546/216, 217, 202, 196, 546/192; 514/327, 320, 324

[56] References Cited

U.S. PATENT DOCUMENTS 4,529,730 7/1985 Schneider et al. ............... 514/327

FOREIGN PATENT DOCUMENTS 0149088 7/1985 European Pat. Off. .
2514353 10/1981 France ................ 514/327

Primary Examiner—Glennon H. Hollrah
Assistant Examiner—Shailendra Kumar
Attorney, Agent, or Firm—Gordon W. Hueschen

[57] ABSTRACT

The compounds disclosed are 1-R'-4-RS-piperidines in which R' and R, which are different, may each represent: (1) (alkoxybenzyl)-alkyl or -alkenyl, or (2) (optionally-substituted chromanyl-, thiochromanyl-, chromenyl- or thiochromenyl)-alkyl or -alkenyl. The compounds are useful in the treatment of disorders associated with tissue ischaemia and of peripheral vascular disorders or in the treatment of disorders in which lipid peroxidation plays an initiating and/or aggravating role. A typical disclosed compound is: 4-(2,3,4-trimethoxybenzylthio)-1-(3,5-di-tert-butyl-4-hydroxybenzyl)piperidine.

5 Claims, No Drawings

PIPERIDINE COMPOUNDS

The present invention provides piperidine compounds of the general formula I:

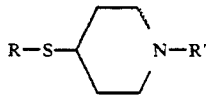
(I)

in which one of the substituents R and R' represents the radical of the formula:

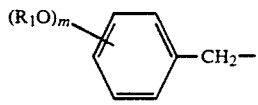

in which
  m is an integer of from 1 to 3 and
  $R_1$ represents an alkyl radical having from 1 to 5 carbon atoms, and
the other substituent R or R' represents:
either a radical of the formula:

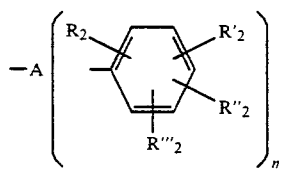

in which:
  A represents a hydrocarbon chain having from 1 to 5 carbon atoms which optionally contains a double bond or an oxygen or sulphur atom and is optionally substituted by a hydroxy radical or by one or more methyl radicals;
  n has the value 1 or 2; and
  each of $R_2$, $R'_2$, $R''_2$ and $R'''_2$, which are identical or different, represents a hydrogen atom, a halogen atom, such as a chlorine or fluorine atom, a straight-chained or branched alkyl or alkoxy radical each having from 1 to 5 carbon atoms, or a hydroxy radical;
or a radical of the formula:

in which:
  Z represents an oxygen or sulphur atom;
  R" represents a hydrogen atom or a methyl radical;
  p has the value 0 or 1; and
  A, $R_2$, $R'_2$, $R''_2$ and $R'''_2$ have the meanings defined above.

The prior art in this field is illustrated especially by the European Patent Application published under no. 0149088, Which relates to compounds of the general formula:

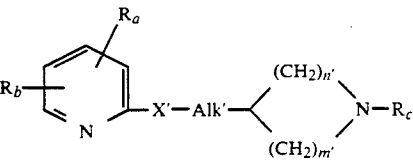

in which:
  $R_a$ and $R_b$ are standard substituents,
  X' is, inter alia, sulphur,
  Alk' is an alkylene chain having from 0 to 4 carbon atoms,
  n' and m', which are identical or different, are integers of from 1 to 3, and
  $R_c$ is, inter alia, hydrogen, $(C_1-C_6)$-alkyl, $(C_3-C_6)$-alkenyl, $(C_3-C_6)$-alkynyl, $(C_3-C_7)$-cycloalkyl or $(C_3-C_7)$-cycloalkenyl;
which compounds have analgesic properties.

That European patent neither describes nor proposes the piperidine compounds forming the subject of the present invention, which are used in the treatment of disorders associated with tissue ischaemia, which is not the case with the compounds of the prior art mentioned above.

The present invention relates also to a process for the preparation of the compounds of the general formula I, which process is characterised in that a compound of the general formula II:

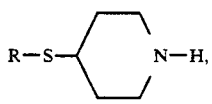
(II)

in which R has the meaning defined above, is condensed with a compound of the general formula III:

Y—R'  (III), in which R' has the meaning defined above and Y represents a chlorine or bromine atom or a tosyloxy radical.

It is especially suitable to carry out the condensation in a polar solvent, such as, for example, a low molecular weight alcohol, dimethylformamide or dimethylacetamide, or in a polar aprotic solvent, such as, for example, acetonitrile or methyl ethyl ketone, in the presence of an acceptor for the hydracid formed during the reaction, at a temperature of from 80° to 130° C.

The starting materials of the general formula II can be prepared by the method described in European Patent No. 0149088 starting from the compound of the formula IV:

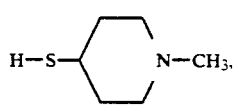
(IV)

which is itself prepared in accordance with the method of H. BARRERA and R. LYLE, J. Org. Chem. 27, 641–643 (1962).

The most suitable method consists in condensing a halide of the formula III with the compound of the formula IV into which sodium has previously been introduced by means of an alkali metal hydride in a polar aprotic solvent, such as dimethylformamide or dimethylacetamide, or by means of an alkali metal alcoholate in a low-boiling alcohol, the respective solvents serving as the reaction medium, at temperatures of from 80° to 130° C.

The resulting compounds of the general formula V:

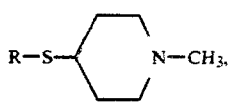 (V)

in which R has the meaning defined above, are converted into compounds of the general formula VI:

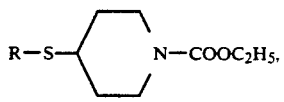 (VI)

in which R has the meaning defined above, which compounds VI are hydrolysed by means of concentrated HCl or ISi(CH$_3$)$_3$ in an aprotic solvent to give the compounds of the general formula II.

The compounds of the general formula I were likewise prepared in accordance with a variant of the method described above.

This process, which is also included in the present invention, is characterised in that a compound of the general formula IIa:

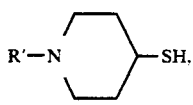 (IIa)

in which R' has the meaning defined above, is condensed with a compound of the general formula IIIa:

Y—R (IIIa), in which Y and R have the meanings defined above.

It is especially suitable to carry out the condensation in a polar solvent, such as a low-boiling alcohol, acetyl cyanide, methyl ethyl ketone, dimethylformamide or dimethylacetamide, at a temperature of from 80° to 110° C., in the presence of an alkaline agent, such as, for example, sodium carbonate or potassium carbonate.

The condensation may also be carried out starting from the compound IIa into which sodium has previously been introduced by means of sodium alcoholate or sodium hydride.

The compounds of the general formula I obtained in accordance with the above methods may be purified by crystallisation in the salt or base form, or by flash chromatography on silica (35–70μ) separated by systems such as, for example, ethyl acetate-acetone, ethyl acetate-methanol, ethyl acetate-dichloromethane, dichloromethane-methanol or dichloromethane-cyclohexane.

The compounds of the general formula I yield salts with physiologically tolerable acids. These salts are also included in the present invention.

The compounds of the present invention have valuable pharmacological and therapeutic properties. In particular, the following properties have been demonstrated for these compounds, in vitro: protection of cells with respect to the consequences of intracellular acidosis, and inhibition of the slow calcium channels; and in vivo: prevention and limitation of the effects induced by myocardial ischaemia.

These properties allow the compounds of the present invention to be used as medicaments in the treatment of disorders associated with tissue ischaemia, especially in the cardiovascular field: angina pectoris, myocardial infarct, the consequences of ischaemic cardiopathies; and in the treatment of peripheral vascular disorders.

The compounds of the present invention may also be used in the cerebral field, especially for the treatment of cerebrovascular accident and the symptoms of deficiency associated with chronic cerebral circulatory disorders; in the field of ophthalmology, especially for the treatment of retinal disorders of vascular origin; and in neurosensory symptoms of ischaemic origin.

Moreover, there has been demonstrated for certain compounds an ability, in vitro, on the one hand to protect human LDL's (low density lipoproteins which serve to transport cholesterol) with respect to the oxidative modifications involved in atherogenesis, and on the other hand to protect cardiac cells with respect to oxidative necrosis.

These properties render the products especially valuable for the prevention or treatment of disorders in which lipid peroxidation plays an initiating and/or aggravating role: such as, for example, atherosclerotic vascular lesions, especially within the context of dyslipidaemias, ischaemic cardiopathies, the reperfusion of organs, including transplanted organs, ischaemic, traumatic or degenerative disorders of the central or peripheral nervous system, acute or chronic inflammatory diseases, and auto-immune diseases.

The present invention relates also to pharmaceutical compositions containing as active ingredient a compound of the general formula I or a physiologically tolerable salt thereof, in admixture or in association with a suitable pharmaceutical excipient, such as, for example, glucose, lactose, starch, talcum, ethyl cellulose, magnesium stearate or cocoa butter.

The pharmaceutical compositions so obtained are generally in dosage unit form and may contain from 1 to 200 mg of active ingredient. They may be in the form of, for example, tablets, dragées, soft gelatine capsules, suppositories or injectable or drinkable solutions and, depending on each particular case, they may be administered orally, rectally or parenterally in a dose of from 1 to 200 mg two or three times per day.

The following Examples illustrate the present invention, melting points being determined using the Kofler hot plate unless indicated otherwise.

EXAMPLE 1

4-(2,3,4-trimethoxybenzylthio)-1-cinnamylpiperidine

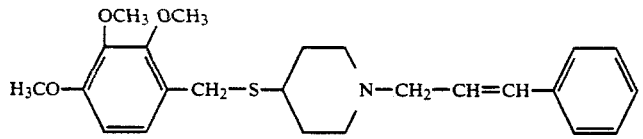

A mixture of 10 g of 4-(2,3,4-trimethoxybenzylthio)-piperidine and 6.62 g of cinnamyl bromide in 300 ml of $CH_3CN$ is heated under reflux for 15 hours in the presence of 4.64 g of potassium carbonate and 0.5 g of potassium iodide. The salt is then filtered off and the filtrate is evaporated under reduced pressure. The residue is taken up in $CH_2Cl_2$—$H_2O$ and, after decantation, the ichloromethane phase is dried over $Na_2SO_4$ and evaporated under reduced pressure. The resulting residue (15 g) is purified by chromatography on 600 g of silica with a toluene-methanol (95-5) system, yielding 10 g of crude base, which is converted into the fumarate in an ethanol medium. 7 g of 4-(2,3,4-trimethoxybenzylthio)-1-cinnamylpiperidine fumarate are obtained in the form of white crystals which melt at 129° C.

The 4-(2,3,4-trimethoxybenzylthio)piperidine used as starting material, the fumarate of which melts at 154° C., was prepared by the hydrolysis, using potassium hydroxide and ethanol, of 4-(2,3,4-trimethoxybenzylthio)-1-ethoxycarbonylpiperidine (oil), which was itself prepared by the action of $ClCOOC_2H_5$ in benzene on 4-(2,3,4-trimethoxybenzylthio)-1-methylpiperidine (m.p. of the corresponding fumarate: 130° C.), which was itself prepared by the condensation of 2,3,4-trimethoxybenzyl chloride in ethanol with the sodium salt of 1-methyl-4-mercaptopiperidine, b.p./$_{13}$ : 70°-72° C.

The compounds forming the subject of Examples 2 to 30 were prepared in the same manner:

EXAMPLES 2-30

2) 4-(2,3,4-trimethoxybenzylthio)-1-bis-p.-fluorobenzhydrylpiperidine and the fumarate thereof m.p.: 179° C. (ethanol/ether).

3) 4-(2,3,4-trimethoxybenzylthio)-1-(2-benzofuranylmethyl)piperidine and the hydrochloride thereof m.p.(cap.): 165° C. (ethanol).

4) 4-(2,3,4-trimethoxybenzylthio)-1-(5-fluoro-2-benzofuranylmethyl)piperidine and the hydrochloride thereof m.p.: 188° C. (ethanol).

5) 4-(2,3,4-trimethoxybenzylthio)-1-(2-benzothienylmethyl)piperidine, m.p.: 115° C.

6) 4-cinnamylthio-1-(2,3,4-trimethoxybenzyl)piperidine and the fumarate thereof m.p.: 165° C. (ethanol).

7) 4-(2,3,4-trimethoxybenzylthio)-1-(4-fluorocinnamyl)piperidine and the hydrochloride thereof m.p.: 164° C. (ethanol/ether).

8) 4-(3,4,5-trimethoxybenzylthio)-1-cinnamylpiperidine, m.p.: 92° C.

9) 4-(2,3,4-trimethoxybenzylthio)-1-(3-Δ3-chromenylmethyl)piperidine and the hydrochloride thereof m.p.: 202° C. (ethanol).

10) 4-(2,4,5-trimethoxybenzylthio)-1-cinnamylpiperidine, m p.: 105° C.

11) 4-benzhydrylthio-1-(2,3,4-trimethoxybenzyl)piperidine and the fumarate thereof m.p.: 105° C. (ethanol).

12) 4-bis-p.-fluorobenzhydrylthio-1-(2,3,4-trimethoxybenzyl)-piperidine and the fumarate thereof m.p.(cap.): 170°-172° C (ethanol).

13) 4-(2,3,4-trimethoxybenzylthio)-1-(3,5-di-tert.-butyl-4-hydroxybenzyl)piperidine and the fumarate thereof m.p.: 202° C.

14) 4-(2,3,4-trimethoxybenzylthio)-1-[3-(3,5-di-tert.-butyl-4-hydroxyphenoxy)propyl]piperidine and the fumarate thereof m.p.(cap.): 156°-158° C.

15) 4-(2,3,4-trimethoxybenzylthio)-1-[3-(3,5-di-tert.-butyl-4-hydroxyphenyl)propyl]piperidine and the fumarate thereof m.p.(cap.): 143°-145° C.

16) 4-(2,3,4-trimethoxybenzylthio)-1-[3-(3,5-di-tert.-butyl-4-hydroxyphenylthio)-2-hydroxypropyl]piperidine and the fumarate thereof m.p.: 120° C.

17) 4-(2,3,4-trimethoxybenzylthio)-1-[3-(3,5-di-tert.-butyl-4-hydroxyphenoxy)-2-hydroxypropyl]piperidine and the fumarate thereof m.p.: 160° C.

18) 4-(2,3,4-trimethoxybenzylthio)-1-[3-(3,5-di-tert.butyl-4-hydroxyphenylthio)propyl]piperidine and the fumarate thereof m.p.: 135° C.

19) 4-(2,3,4-trimethoxybenzylthio)-1-[3-(2,3,5-trimethyl-4-hydroxyphenoxy)propyl]piperidine and the fumarate thereof m.p.: 164° C.

20) 4-(2,3,4-trimethoxybenzylthio)-1-[5-(3,5-di-tert.butyl-4-hydroxyphenylthio)pentyl]piperidine and the fumarate thereof m.p.: 138° C.

21) 4-(2,3,4-trimethoxybenzylthio)-1-[5-(3,5-di-tert.-butyl-4-hydroxyphenoxy)pentyl]piperidine and the fumarate thereof m.p.: 142° C.

22) 4-(2,3,4-trimethoxybenzylthio)-1-[3-(3,5-di-tert.-butyl-4-hydroxyphenylthio)-3-methylbutyl]piperidine.

23) 4-(2,3,4-trimethoxybenzylthio)-1-[3-(3,5-di-tert.-butyl-4-hydroxyphenoxy)-3-methylbutyl]piperidine.

24) 4-(2,3,4-trimethoxybenzylthio)-1-[3-(2,3,5-trimethyl-4-hydroxyphenoxy)-3-methylbutyl]piperidine.

25) 4-(2,3,4-trimethoxybenzylthio)-1-[3-(3,5-di-tert.-butyl-4-hydroxyphenylthio)-2,2-dimethylpropyl]-piperidine.

26) 4-(2,3,4-trimethoxybenzylthio)-1-[3-(3,5-di-tert.-butyl-4-hydroxyphenoxy)-2,2-dimethylpropyl]piperidine.

27) 4-(2,3,4-trimethoxybenzylthio)-1-[3-(2,3,5-trimethyl-4-hydroxyphenoxy)-2,2-dimethylpropyl]piperidine.

28) 4-(2,3,4-trimethoxybenzylthio)-1-[(2-methyl-5,7,8-trimethyl-6-hydroxy-2-chromanyl)methyl]piperidine.

29) 4-(2,3,4-trimethoxybenzylthio)-1-[2-(2-methyl-5,7,8-trimethyl-6-hydroxy-2-chromanyl)ethyl]piperidine.

30) 4-(2,3,4-trimethoxybenzylthio)-1-[3-(2-methyl-5,7,8-trimethyl-6-hydroxy-2-chromanyl)propyl]piperidine.

EXAMPLE 31

4-(2,3,4-trimethoxybenzylthio)-1-bis-p.-fluorobenzhydrylpiperidine

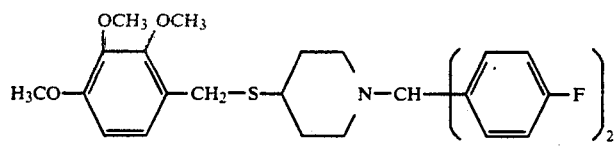

0.5 g of 50% sodium hydride in oil is added to a solution of 3.2 g of 4-mercapto-1-bis-p.-fluorobenzhydrylpiperidine in 50 ml of dimethylformamide.

The mixture is stirred for one hour, and 2.4 g of 2,3,4-trimethoxybenzyl chloride are added to the resulting solution. The solution is then heated at 80° C. for 3 hours and then cooled, and the dimethylformamide is evaporated off.

The residual phase is treated with water and dichloromethane. The dichloromethane phase is decanted off, and evaporation yields 5 g of crude base which are chromatographed on 200 g of silica using a toluene-methanol mixture (95-5) as eluant.

Finally, 3.5 g of 4-(2,3,4-trimethoxybenzylthio)-1-bis-p.-fluorobenzhydrylpiperidine are collected in the form of a pure base, the fumarate of which, when crystallised in ethanol, melts at 179° C. The 4-mercapto-1-bis-p.-fluorobenzhydrylpiperidine (oil) used as starting material was prepared analogously to the method of H. BARRERA et al., J. Org. Chem. 27, 641–643 (1962) starting from 1-benzhydryl-4-piperidone which melts at 108° C.

The starting materials (II) used for the synthesis of the compounds exemplified above are listed in the following Table:

Compounds of the formula:

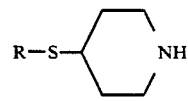

| R | m.p. °C. (Kofler) |
|---|---|
| 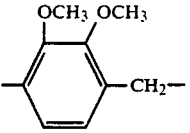 2,3,4-trimethoxybenzyl | 72 |
| 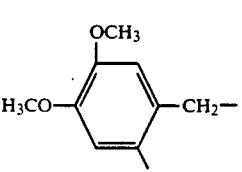 3,4,5-trimethoxybenzyl variant | oil |
|  cinnamyl | ≈35 |
|  benzhydryl | 74–76 |

The halogenated starting materials or tosyloxy starting materials used for the synthesis of the compounds exemplified above are listed in the following Table.

| Compounds | m.p. °C. (Kofler) | Method of preparation |
|---|---|---|
| 3,5-di-tert-butyl-4-hydroxyphenyl-(CH₂)₃-Br | 58–60 (cap) | Bromination of the alcohol with (C₆H₅)₃PBr in DMF |
| 3,5-di-tert-butyl-4-hydroxyphenyl-O-(CH₂)₃-Br | 35–36 | |

-continued

| Compounds | m.p. °C. (Kofler) | Method of preparation |
|---|---|---|
| 2,6-di-tert-butyl-4-(5-bromopentyloxy)phenol (HO-C₆H₂(C(CH₃)₃)₂-O-(CH₂)₅-Br) | oil | ![reaction scheme] HO-C₆H₂(C(CH₃)₃)₂-XH + Br(CH₂)ₘBr $\xrightarrow{K_2CO_3 / AcCN}$ |
| 2,6-di-tert-butyl-4-(3-bromopropylthio)phenol (HO-C₆H₂(C(CH₃)₃)₂-S-(CH₂)₃-Br) | oil | |
| 2,6-di-tert-butyl-4-(5-bromopentylthio)phenol (HO-C₆H₂(C(CH₃)₃)₂-S-(CH₂)₅-Br) | oil | HO-C₆H₂(C(CH₃)₃)₂-XH + Br(CH₂)₅Br $\xrightarrow{K_2CO_3 / AcCN}$ |
| HO-C₆H₂(C(CH₃)₃)₂-S-CH₂-CH(OH)-CH₂-Cl | 68 | |
| HO-C₆H₂(C(CH₃)₃)₂-S-CH₂-CH(OH)-(CH₂)₂-Br | 125 | |
| (H₃C)₃C-Si-O-C₆(CH₃)₄-O-(CH₂)₃-Br | 45–46 | according to T. YOSMIOKA et al. J. Med. Chem. 32, 421–428 (1989) |
| C₂H₅O-CH₂-O-[tetramethyl tetrahydronaphthyl]-(CH₂)₂-tosyloxy | oil | Tosylation of the alcohol prepared according to J. Scott et al., J. Am. Oil. Chem. Soc. 51, (5), 200–203, (1974) |
| CH₃-COO-[tetramethyl tetrahydronaphthyl]-(CH₂)₂-Br | 102–103 | According to MERREL E.P. 369,874 |

| Compounds | m.p. °C. (Kofler) | Method of preparation |
|---|---|---|
| 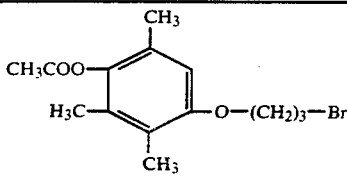 | 54 | 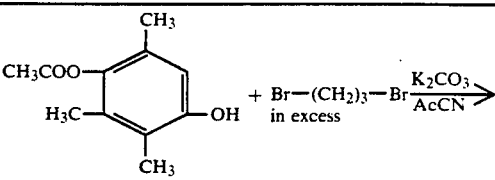 |

EXAMPLE 32

Pharmacological Study

A) IN VITRO STUDY

I. Protection with Respect to Intracellular Acidosis and Inhibition of the Slow Calcium Channels The action of the compounds of the present invention and in particular of the compound of Example 1 was demonstrated on cardiac cells of rats. The cell-protective effects with respect to the events associated with intracellular acidosis (ischaemia-anoxia) and the inhibitory effect on the entry of calcium through the slow calcium channels were demonstrated. The protective effects of the compound of Example 1 were evaluated with respect to the primary sequence of the necrosing events induced during ischaemia, and in comparison with those of trimetazidine dihydrochloride (DCI) and cinnarizine (DCI) as reference product.

α) Materials and methods

Cell culture a) Cardiac cells: the cardiac cells are prepared from the hearts of newly born (3 days) Wistar rats in accordance with the technique of RENAUD JF., MEAUX JP., ROMEY G., SCHMID A., LAZDUNSKI M., Activation of the voltage-dependent $Ca^{2+}$ channels in rat heart cells by dihydropyridine derivative—Biochem. Biophys. Res. Commun., 125, 405–412 (1984).

The cardiomyocytes are isolated from the ventricles by enzymatic dissociation and cultured at 185,000 cells/$cm^2$. The cells are kept at 37° C. under an air/-$CO_2$ atmosphere (95 V/5 V) saturated with water. The cardiomyocytes are used between the 3rd and 8th day following culturing.

b) $A_7r_5$: cell lines from the aorta of newly born rats (ATCC No. CRL 1444), cultivated under the conditions indicated by the American Type Culture Collection (ATCC).

Binding study

The binding studies are carried out on microsomal fractions enriched with type L calcium channels [cf. FOSSET M., LAZDUNSKI M., Biochemical characterization of the skeletal muscle $Ca^{2+}$ channel. In: Receptors Biochemistry and Methodology, Venter J. C., Triggle D., eds., vol. 9, 141–159 (1986) and O'BRIEN R. A., Receptor binding in drug research. In: Clinical Pharmacology, vol. 5 (1986)].

The competition experiments between the different radioligands and the reference molecules are carried out under the standard binding conditions according to O'BRIEN R. A., Receptor binding in drug research. In: Clinical Pharmacology, vol. 5, DEKKER M. Inc., New York and Basle (1986). In all cases, after the required linkage time, the bound radioactivity is separated from the free component by in vacuo filtration on a GF/C filter.

Ionic flux

The influx of $^{45}Ca^{2+}$ is evaluated on the $A_7r_5$'s in the presence or absence of D 888 (specific inhibitor of the type L $Ca^{2+}$ channel) and in the presence or absence of variable concentrations of the compound of Example 1, under the conditions published on the heart by RENAUD JF., KAZASOGLOU T., SCHMID A., ROMEY G., LAZDUNSKI M., Differentiation of [3H] nitrendipine receptor sites in chick hearts and physiological relation to the slow $Ca^{2+}$ channel and to excitation-contraction coupling. Eur. J. Biochem., 139 673–681 (1984).

Electrophysiology

The studies were carried out on the $A_7r_5$ cell line using the whole cell patch-clamp technique described by HAMILL O., MARTY A., WEHER E., SAKMANN B., SIGWORTH F. F., Improved patch clamp techniques for high resolution current recording from cells and cell from membrane patches. Pflügers Arch., 391, 85–100 (1981).

Measurement of the protection index after induction of intracellular acidosis

Intracellular acidosis is induced in accordance with the conditions published by RENAUD JF., Internal pH $Na^+$ and $Ca^{2+}$ regulation by trimetazidine during cardiac cell acidosis. Cardiovasc. Drugs and Ther., 1, 667–686 (1988) in the presence or absence of the products to be tested. Cellular necrosis is evaluated by measuring by spectrophotometry using the Boerhinger 124800 kit the kinetics of the release of a cytosolic enzyme α-hydroxybutyrate dehydrogenase (αHBDH) into the extracellular medium.

β) Results

1) Effect of the compound of Example 1 on the fixation of PN 200-110 and of D888 at the level of the $Ca^{2+}$ channel.

Comparison with trimetazidine dihydrochloride and cinnarizine.

| | Reference $K_{0.5}$ (M) | Compound of Example 1 $K_{0.5}$ (M) | Trimetazidine, 2 HCl $K_{0.5}$ (M) | Cinnarizine $K_{0.5}$ (M) |
|---|---|---|---|---|
| [3H] PN 200-110 | Nifedipine $2.5 \times 10^{-8}$ | $10^{-6}$ | $>10^{-4}$ | $3.4 \times 10^{-7}$ |
| [3H] D888 | D888 $2.5 \times 10^{-9}$ | $1.3 \times 10^{-6}$ | $>10^{-4}$ | $5.2 \times 10^{-7}$ |

The $K_{0.5}$ values are expressed as molar values (mole/l) and correspond to the concentration for which 50% of the radioactivity fixed in specific manner is displaced by the product under consideration.

2) Effect of the compound of Example 1 on the inhibition of the influx of $Ca^{2+}$ passing through the $Ca^{2+}$ channel.

Comparison with trimetazidine dihydrochloride and cinnarizine.

|  | Reference $K_{0.5}$ (M) | Compound of Example 1 $K_{0.5}$ (M) | Trimetazidine, 2 HCl $K_{0.5}$ (M) | Cinnarizine $K_{0.5}$ (M) |
|---|---|---|---|---|
| D888 | $2.3 \times 10^{-8}$ | $3 \times 10^{-6}$ | $>10^{-4}$ | $1.2 \times 10^{-7}$ |

The $K_{0.5}$ values are expressed as molar values (mole/l) and correspond to the concentration for which 50% of the influx of $^{45}Ca^{2+}$ passing through the $Ca^{2+}$ channel is inhibited by the product under consideration.

3) Effect of the compound of Example 1 on neurotransmitter receptors. Comparison with trimetazidine dihydrochloride (see following Table).

$Ca^{2+}$ channel and that this binding leads on the one hand to inhibition of the influx of $Ca^{2+}$ and on the other hand to inhibition of the $Ca^{2+}$ entry flow in a dose-dependent manner.

These results distinguish the compound of Example 1 from trimetazidine dihydrochloride on account of its calcium-blocking properties and show that it is similar to cinnarizine and has a good dose-effect relationship. The results given in 3 show that the compound of Example 1 interacts in a relatively non-specific manner and with low affinity with neurotransmitter receptors (5HT, $\alpha, \beta$) with the exception of the dopaminergic receptors. The results given in 4 show that the compound of Example 1 protects the cardiac cell from necrosis induced

| Receptors | Ligand | Reference | $K_{0.5}$ (M) | Compound of Example 1 $K_{0.5}$ (M) | Trimetazidine 2 HCl $K_{0.5}$ (M) | Cinnarizine $K_{0.5}$ (M) |
|---|---|---|---|---|---|---|
| Serotonin |  |  |  |  |  |  |
| $5HT_{1A}$ | [3H] 8 OH DPAT | 8 OH DPAT | $3 \times 10^{-9}$ | $3 \times 10^{-6}$ | $10^{-4}$ | $4 \times 10^{-6}$ |
| $5HT_{1B}$ | [125] CYP | Serotonin | $3.5 \times 10^{-8}$ | $10^{-5}$ | $10^{-4}$ | $10^{-4}$ |
| $5HT_2$ | [3H] Ketanserine | Ketanserine | $8.2 \times 10^{-9}$ | $10^{-6}$ | $>10^{-4}$ | $10^{-6}$ |
| Alpha adrenergic |  |  |  |  |  |  |
| $\alpha 1$ | [3H] Prazosin | Prazosin | $6.10^{-10}$ | $2 \times 10^{-6}$ | / | $4 \times 10^{-7}$ |
| $\alpha 2$ | [3H] Rauwolscine | Yohimbine | $3.1 \times 10^{-8}$ | $9 \times 10^{-7}$ | / . | $2 \times 10^{-6}$ |
| Beta adrenergic |  |  |  |  |  |  |
| $\beta$ | [3H] DHA | Alprenolol | $2.1 \times 10^{-9}$ | $2 \times 10^{-6}$ | $>10^{-4}$ | $>10^{-4}$ |
| Dopamine |  |  |  |  |  |  |
| $D_1$ | [3H] SCH 23390 | SCH 23390 | $7 \times 10^{-10}$ | $3 \times 10^{-7}$ | / | $3 \times 10^{-7}$ |
| $D_2$ | [3H] 205 501 | Butaclamol | $10^{-9}$ | $3 \times 10^{-7}$ | / | $10^{-7}$ |

4) Protective effect of the compound of Example 1 on the consequences associated with intracellular acidosis.
Comparison with trimetazidine dihydrochloride.

by intracellular acidosis. This protection occurs at $1 \mu M$ and above and reaches a maximum between 3 and $10 \mu M$ of compound of Example 1 with 99 to 98% protectin.

| Concentrations $\mu M$ | 0.3 | 1 | 3 | 10 | 20 | 30 | 100 | 500 |
|---|---|---|---|---|---|---|---|---|
| Compound of Example 1 | 143.99 ± 26.72 (n = 4) | 21.95 ± 1.19 (n = 4) | 1.42 ± 0.74 (n = 4) | 2.14 ± 0.8 (n = 4) | / | 9.68 ± 2.69 (n = 4) | / | / |
| Triametazidine 2 HCl | / | / | / | / | 94.58 ± 12.53 (n = 3) | / | 75.76 ± 7.79 (n = 3) | 58.26 ± 8.13 (n = 3) |
| control before acidosis |  |  |  |  | 0% ± 0.86 n = 3 |  |  |  |
| control after acidosis alone |  |  |  |  | 100% ± 11.10 n = 4 |  |  |  |

The signal measured corresponds to the amplitude of the necrosis induced by the acidosis. The values are the means ±SD. The number of experiments is indicated in parentheses.

5) Electrophysiological studies carried out on a rat aortic cell line (A7r5).

The studies show under whole cell patch clamp conditions an inhibition of the slow calcium entry flow with a semi-effect ($EC_{50}$) for the compound of Example 1 at $10^{-5}M$.

6) Conclusion:

The results obtained in 1, 2 and 5 show that the compound of Example 1 binds to the receptors of the slow Under the same conditions, trimetazidine dihydrochloride, at a concentration 500 times greater ($500 \mu M$), protects only 42% of a cell population subjected to intracellular acidosis.

II. Protection with Respect to Oxidative Modifications of LDL's and Oxidative Necrosis of Cardiac Cells The activity of the compounds of the present invention was demonstrated in vitro on the oxidative modification of human LDL's induced by copper sulphate, and on the necrosis of cardiac cells.

α) Materials and methods a) Modification of LDL's by copper sulphate

Human LDL's are incubated for 24 hours in the presence of copper sulphate ($5 \times 10^{-6}$M) and in the absence or in the presence of the test compounds ($10^{-7}$M to $10^{-4}$M).

After incubation, the peroxidation of the LDL's is evaluated by agar gel electrophoresis and by the formation of one of the products of lipid peroxidation: malondialdehyde (MDA) (Parthasarathy S., Young S. G., Witztum J. L., Pittman R. C. and Steinberg D.; J. Clin. Invest. 77, 641-644, 1986).

The activity of the compounds tested is evaluated by calculating the concentrations that reduce the production of MDA by 50% ($IC_{50}$) relative to control experiments in the absence of the product.

b) Oxidative necrosis of cardiac cells

Cardiac cells of newly born rats are used between the 5th and 7th day following culturing. Oxidative necrosis is induced by the enzymatic production system of hypoxanthine (HX, 1 mM) and xanthine oxidase free radicals (XO, 10 mU/ml). The necrosis is evaluated 4 hours after the addition of XO/HX by measuring by spectrophotometry the cytosolic α-hydroxybutyrate dehydrogenase (α-HBDH) activity released into the supernatant liquor. Two reference molecules (Probucol, vitamin E) and two molecules representative of the present invention (corresponding to Examples 13 and 19) were tested. The cells are treated with the molecules 16 hours and 1 hour before the start of the experiment after renewal of the medium. At the start of the experiment, the treatment is repeated one last time.

β) Results

1) Effect on the modification of LDL's

The Table below shows the $IC_{50}$'s, evaluating the ability to inhibit the lipid peroxidation of human LDL's, obtained with a sample of compounds of the invention and the anti-oxidant reference products: Probucol and vitamin E, in the test of oxidation of the LDL's with copper sulphate ($Cu^{2+}$).

| Compounds | $IC_{50}$ (M) ($Cu^{2+}$) |
|---|---|
| Example 13 | $3 \times 10^{-6}$ |
| Example 14 | $10^{-6}$ |
| Example 15 | $3 \times 10^{-6}$ |
| Example 16 | $3 \times 10^{-6}$ |
| Example 17 | $2 \times 10^{-6}$ |
| Example 18 | $2 \times 10^{-6}$ |
| Example 19 | $3 \times 10^{-7}$ |
| Example 20 | $10^{-6}$ |
| Example 21 | $8 \times 10^{-7}$ |
| Probucol | $3 \times 10^{-6}$ |
| Vitamin E | $>10^{-4}$ |

These results clearly show the greater ability especially of the compound of Example 19, as compared with Probucol or vitamin E, to protect human LDL's with respect to modifications induced by copper sulphate.

2) Effect on the oxidative necrosis of cardiac cells

The following Table summarises the indices of necrosis of cardiac cells induced by the hypoxanthine/xanthine oxidase system by itself or in the presence of increasing concentrations of the tested compounds of the invention or of the reference products Probucol and vitamin E.

| Compounds | Control XO + HX | $10^{-7}$ M XO + HX | $10^{-6}$ M XO + HX | $10^{-5}$ M XO + HX |
|---|---|---|---|---|
| Example 13 | 100.0 ± 19.2 | 75.7 ± 19.7 | 52.4 ± 18.2 | 16.1 ± 5.6 |
| Example 19 | 100.0 ± 6.8 | 86.0 ± 11.5 | 38.4 ± 13.7 | 7.9 ± 4.1 |
| Probucol | 100.0 ± 11.9 | | 95.0 ± 1.7 | 68.0 ± 0.9 |
| Vitamin E | 100.0 ± 10.6 | 97.1 ± 2.6 | 87.6 ± 5.7 | 54.9 ± 11.3 |

The necrosis index 100 corresponds to the release of 46.7±5.3% of the cytosolic content of α-HBDH into the supernatant liquor in 4 hours.

The results are expressed as the mean ±SD ($2 < n \leq 4$, 3 to 4 repetitions per experiment).

The compounds of Examples 13 and 19, which reduce the oxidative necrosis of the cardiomyocytes by 50% or more from $10^{-6}$M, are markedly superior to the anti-oxidant reference products, whose activity, which is weaker, occurs only at $10^{-5}$M.

B) IN VIVO STUDY

Demonstration of Anti-Ischaemic Activity

1) METHOD

The studies are carried out on beagle dogs weighing from 9 to 12 kg which have been anaesthetised with pentobarbital sodium 30 mg/kg i.v., intubated and ventilated, and subjected to a thoracotomy at the 5th left intercostal space.

An electromagnetic ring connected to a Gould SP 2202 electromagnetic flow meter is placed around the circumflex branch of the left coronary artery, and an inflatable balloon is placed just downstream of that ring for the production of coronary stenoses under the control of the coronary output.

Piezoelectric crystals (5 MHz) connected to a Triton sonomicrometer are implanted in the subendocardium of the left ventricular wall, in an area that is to become ischaemic, for measuring local myocardial contractility; epicardial electrodes are placed in the same area for recording the epicardial electrocardiogram.

Two electrodes are sewn at the right auricle in the region of the sinoauricular node for the protocols including pacing sequences.

2) EXPERIMENTAL PROTOCOLS

Two types of protocol of myocardial ischaemia are carried out:

Protocol 1

Myocardial ischaemia is induced by tight coronary stenosis that reduces coronary output by about 70%.

The same coronary stenosis, the effects of which are reversible and reproducible, is produced in the same animal for two periods of 10 minutes, separated by a recovery period of 45 minutes.

Treatments are administered intravenously 2 minutes after coronary stenosis:

injection of solvent after the first coronary stenosis, which serves as control, injection of the test product after the second coronary stenosis.

Protocol 2

A moderate coronary stenosis that reduces coronary output by 30 to 50%, which in itself is not sufficient to induce ischaemia, is established.

Myocardial ischaemia is induced by accelerating the cardiac frequency by about 90 beats per minute, by means of auricular pacing maintained for a period of 2 minutes.

Two pacing sequences, the effects of which are reversible and reproducible, are carried out on the same animal, the first sequence being preceded by injection of solvent as control and the second, after a recovery period of 45 minutes, being preceded by injection of the product to be tested.

The treatments are administered intravenously 3 minutes before the pacing sequence.

3) PARAMETERS MEASURED

Myocardial contractility is evaluated by the proportion of systolic shortening of the lengths of the segments between the piezoelectric crystals.

Hypokinesia in the ischaemic area is expressed as percentage variation relative to the contractility measured in the control period.

Modification of the epicardial ECG in the ischaemic area consists in raising the epicardial ST segment measured in millivolts (mV).

4) RESULTS

| Parameters | Treatment | Stenosis | 10 minutes after treatment |
|---|---|---|---|
| Protocol 1 | | | |
| Contractility delta % | Solvent | −45.8 | −44.5 |
|  | Compound of Example 1 1 mg/kg i.v. | −45 | −24.3 |
| Epicardial ST delta mV | Solvent | +4.5 | +4 |
|  | Compound of Example 1 1 mg/kg | +4.5 | +2 |

| Parameters | Treatment | Pacing 2 minutes |
|---|---|---|
| Protocol 2 | | |
| Contractility delta % | Solvent | −62.6 |
|  | Compound of Example 1 1 mg/kg i.v. | −42.2 |
| Epicardial ST delta mV | Solvent | +6.0 |
|  | Compound of Example 1 1 mg/kg i.v. | +0.5 |

Conclusion:

When administered intravenously, the compound of Example 1 markedly reduces both preventively and curatively the electrocardiographic modifications and the modifications of myocardial contractility induced by ischaemia.

We claim:

1. A compound selected from the group consisting of: a piperidine compound of the formula I:

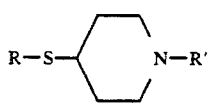

(I)

in which one of the substituents R and R' represents the radical

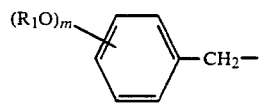

in which,
m is an integer of 1 to 3 and
$R_1$ is an alkyl radical having 1 to 5 carbons atoms, and the other substituent R or R' is selected from the group consisting of
a) a radical of the formula:

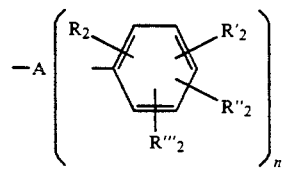

in which:
A is selected from the group consisting of a hydrocarbon chain having 1 to 5 carbon atoms, such chain containing a double bond, such chain interrupted by an oxygen or a sulphur atom, and such chain substituted by hydroxy or by one or more methyl radicals;
n is selected from the values 1 and 2; and
$R_2, R'_2, R''_2$ and $R'''_2$, which are identical or different, are each selected from the group consisting of: hydrogen, halogen, straight-chained and branched alkyl and alkoxy radicals each having 1 to 5 carbon atoms, and hydroxy; and
b) a radical of the formula:

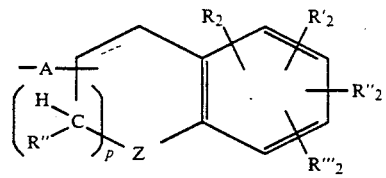

in which:
Z is selected from oxygen and sulphur;
R'' selected from hydrogen and methyl;
p is selected from the values 0 and 1; and
A, $R_2$, $R'_2$, $R''_2$ and $R'''_2$ have the meanings defined above; and
physiologically-tolerable acid addition salts thereof.

2. A compound of claim 1 which is: 4-(2,3,4-trimethoxybenzylthio)-1-cinnamylpiperidine.

3. A compound of claim 1 which is selected from the group consisting of 4-(2,3,4-trimethoxybenzylthio)-1-(3,5-di-tert.-butyl-4-hydroxybenzyl)piperidine and the fumarate thereof.

4. A compound of claim 1 which is selected from the group consisting of 4-(2,3,4-trimethoxybenzylthio)-1-[3-(2,3,5-trimethyl-4-hydroxyphenoxy)propyl]piperidine and the fumarate thereof.

5. A pharmaceutical composition useful in treating tissue ischaemia containing as active ingredient an amount of a compound according to claim 1 effective for such purpose together with a pharmaceutically acceptable carrier.

* * * * *

UNITED STATES PATENT AND TRADEMARK OFFICE
CERTIFICATE OF CORRECTION

PATENT NO. : 5,126,356

DATED : Jun. 30, 1992

INVENTOR(S) : Gilbert Regnier, J. F. Renaud De La Faverie, Alain Lombet,
Jean-Pierre Iliou, Jean-Paul Vilaine, Jean-Pierre Bidourad, Albert Lenaers It is certified that error appears in the above-identified patent and that said Letters Patent is hereby corrected as shown below:

Column 1, line 67; "Which" should read -- which --.
Column 5, line 2; "cinnamylpiperidine" should read
   cinnamylpiperidine: --.
Column 5, line 23; "ichloromethane" should read
   -- dichloromethane --.
Column 14, third line under the second table; "protectin."
   should read -- protection. --.

Signed and Sealed this

Thirty-first Day of August, 1993

*Attest:*

BRUCE LEHMAN

*Attesting Officer*   *Commissioner of Patents and Trademarks*